US00PP20364P2

(12) United States Plant Patent
Egger

(10) Patent No.: US PP20,364 P2
(45) Date of Patent: Sep. 29, 2009

(54) ***HEUCHERA* PLANT NAMED 'SOUTHERN COMFORT'**

(50) Latin Name: ***Heuchera* spp**
Varietal Denomination: Southern Comfort

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/157,779

(22) Filed: Jun. 12, 2008

(51) Int. Cl.
*A01H 5/00* (2006.01)

(52) U.S. Cl. ..... Plt./440

(58) Field of Classification Search ..... Plt./440
See application file for complete search history.

*Primary Examiner*—Annette H Para
*Assistant Examiner*—Louanne C Krawczewicz Myers
(74) *Attorney, Agent, or Firm*—Klarquist Sparkman, LLP

(57) ABSTRACT

A new and distinct hybrid of *Heuchera* plant characterized by very large, pubescent leaves, amber leaf color, and excellent vigor.

1 Drawing Sheet

Botanical classification: *Heuchera* spp.

Variety denomination: 'Southern Comfort'.

The present invention relates to a new and distinct cultivar of *Heuchera* hybrid and given the cultivar name of 'Southern Comfort'. *Heuchera* is in the family Saxifragaceae. *Heuchera* 'Southern Comfort' originated as controlled cross between *Heuchera* 'Sparkling Burgundy' (U.S. Plant Pat. No. 17,208), as the seed parent and *Heuchera villosa* (unpatented), as the pollen parent. Of all the offspring, *Heuchera* 'Southern Comfort' was selected for its vigor, leaf color, and large, lush leaf size.

This new and unique *Heuchera* is distinguished by:

1. very large, pubescent leaves,
2. amber leaf color,
3. and excellent vigor.

This new cultivar has been reproduced only by asexual propagation (cuttings and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a one-year-old *Heuchera* 'Southern Comfort' growing in the ground in the shade house in April in Canby, Oreg.

FIG. 2 shows a two-year-old *Heuchera* 'Southern Comfort' growing in the ground in the shade house in June in Canby, Oreg.

DETAILED PLANT DESCRIPTION

The following is a detailed description of the new *Heuchera* cultivar based on observations taken in October of a two-year-old specimen grown in the ground in a shade house with 50% shade cover and added irrigation in the summer months in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, 1999 edition.

Botanical classification: *Heuchera* spp.

Variety denomination: 'Southern Comfort'

Plant:

- *Form.*—Basal rosette, herbaceous perennial.
- *Hardiness.*—USDA Zone 4 to 9.
- *Size.*—37 cm tall from the ground to the top of the foliage and 70 cm wide.
- *Habit.*—Mounding.
- *Vigor.*—Excellent.
- *Roots.*—Fibrous, freely branching, fine, and white in color; roots develop easily from stem tip cuttings.

Lateral branches: None.

Leaf:

- *Type.*—Simple.
- *Arrangement.*—Rosette.
- *Shape.*—Broadly ovate to orbicular.
- *Lobing /division.*—5 rounded lobes, the terminal and longest, shallow secondary lobes.
- *Leaf quantity.*—Average 27 to 35 leaves for a one year old plant.
- *Venation.*—Palmate.
- *Venation color (upper surface).*—Greyed Yellow 161C.
- *Venation color (lower surface).*—Greyed Orange 177D.
- *Margins.*—Broadly crenate, slightly undulate.
- *Apex.*—Mucronulate.
- *Base.*—Cordate, overlapping, lobes curling upward.
- *Blade size.*—Grows to 17.5 cm long and 16 cm wide.
- *Surface texture.*—Strongly hirsute on both sides.
- *Petiole description.*—Grows to 25 cm long and 4 mm wide, strongly glandular hirsute, Greyed Orange 177A.
- *Leaf color.*—Variable depending on maturity, temperature, light, and season; topside in spring leaves first appear Greyed Purple 186B, changing to Greyed Red 182B then Greyed Orange 174A and 174B; bottom side spring Greyed Purple 185B; summer and fall colors are the same on the newer leaves with the older and winter leaves topside darkening to Greyed Orange 166A and lightening to Greyed Orange 165B; bottom side summer, fall and winter Greyed Purple 185B.

Inflorescence:

*Type.*—Thyrse.

*Number of thyrse per plant.*—About 5.

*Inflorescence length and width.*—Grows to 22 cm long and 17 mm *wide*.

*Number of flowers.*—About 100 per thyrse.

*Peduncle description.*—Unbranched, with 2 or 3 sessile bracts per scape, bracts grow to 2 cm long and 1 cm wide, ovate, serrate, with 3 to 5 main lobes, Greyed Orange 174A; peduncle grows to 65 cm tall and 4 mm wide, glandular puberulent, Greyed Purple 183A.

*Pedicel description.*—3 mm long and 0.5 mm wide, glandular puberulent, Greyed Purple 183A.

*Bloom period.*—May to July in Canby, Oreg.

Flower bud:

*Size.*—3 mm long, 2 mm wide.

*Description.*—Glandular puberulent, ovoid.

*Color.*—Greyed Yellow 160D.

Flower:

*Type.*—Perfect, zygomorphic.

*Shape.*—Campanulate.

*Size.*—5 mm long and 3 mm wide.

*Petal description.*—5, inconspicuous, 4 mm long and 0.8 mm wide, lanceolate with a clawed base, strongly reflexed, entire, acute, White 155D and glabrous on both sides.

*Calyx description.*—4 mm deep and 3 mm wide, urceolate, with 5 lobes divided ⅓ to the base, long glandular hairs on outside, glabrous inside, entire, acute, Yellow Green 152A inside and on lobes inside and out, Yellow Green 145C on lobe tips and base with White 155A in between.

*Stamen.*—5, about 2 mm long, filaments Yellow Green 145D, 1.6 mm long, anthers sterile, 0.4 mm long, Greyed Orange 165A, no pollen.

*Pistil.*—1, 4 mm long, Yellow Green 145C overall, ovary 2 mm long and 2 beaked style 2 mm long.

*Fragrance.*—None.

*Lastingness.*—Each thyrse blooms for about 2 weeks on the plant.

Fruit:

*Type.*—Two-beaked ovoid capsule.

*Fertility.*—Good.

*Size.*—About 4.5 mm long and 2.5 mm wide.

*Color.*—Tan. RHS 160C Greyed-Yellow to 199C Grey-Brown.

Seed:

*Shape.*—Linear.

*Size.*—2 mm long.

*Color.*—Black RHS 202A.

Disease and pest tolerance: Excellent disease resistance to powdery mildew, the common problem of *Heuchera*. Susceptible to root weevils. Not highly susceptible to *Heuchera* rust.

COMPARISON TO SIMILAR *Heuchera*

Compared to *Heuchera* 'Sparkling Burgundy' (U.S. Plant Pat. No. 17,208), the seed parent, the new variety has larger, more pubescent leaves, of amber shades rather than burgundy.

Compared to the pollen parent, *Heuchera villosa*, the new variety has amber rather than green leaves.

Compared to *Heuchera* 'Caramel' (U.S. Plant Pat. No. 16,560), the new variety has larger leaves and a larger habit as well as more variable leaf color.

I claim:

1. A new and distinct hybrid of *Heuchera* plant, named 'Southern Comfort', substantially as shown and described.

* * * * *

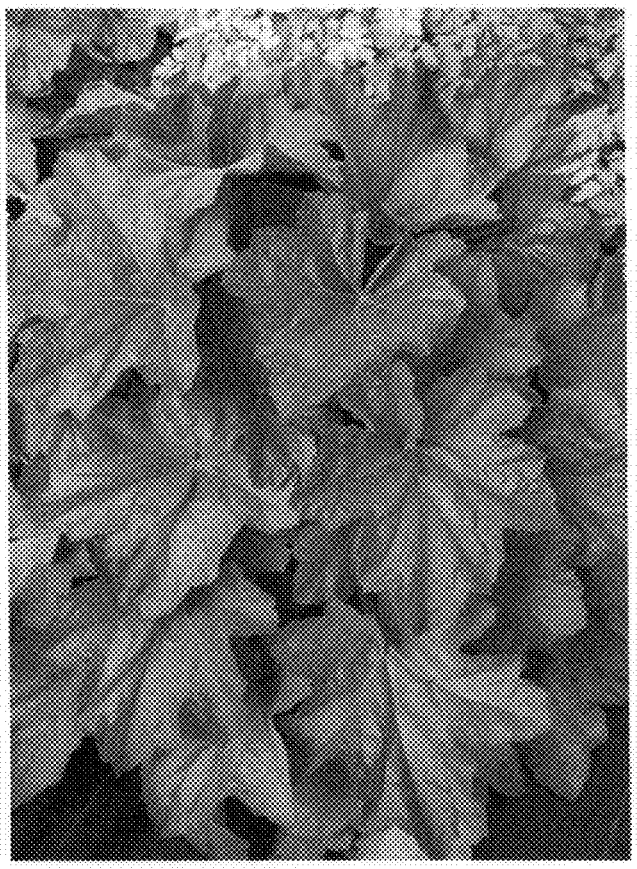

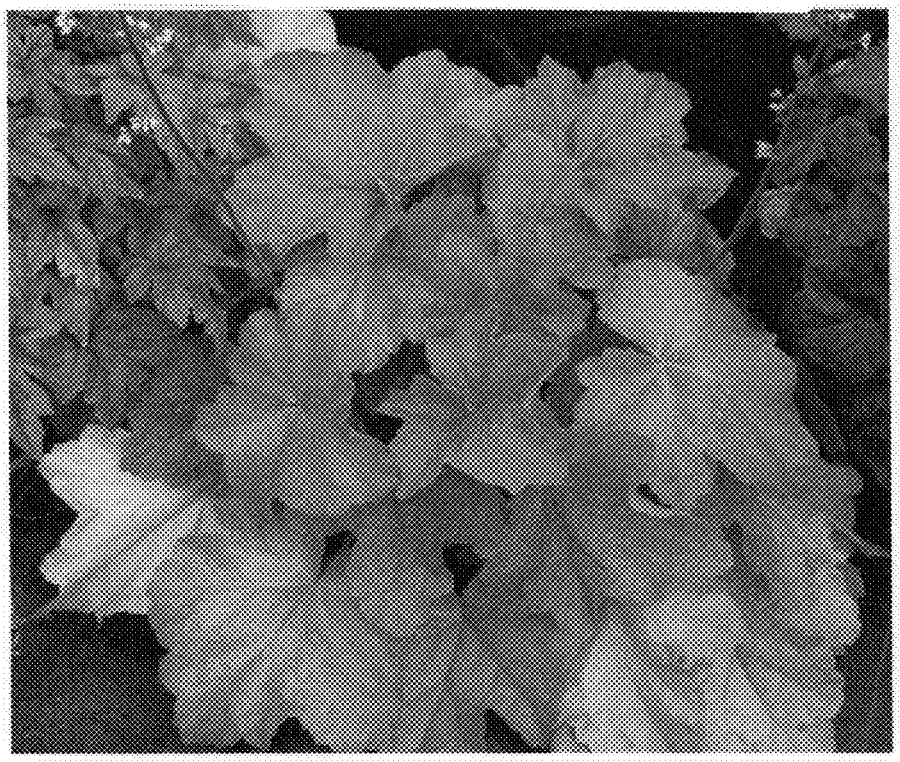
Figure 1 above
Figure 2 right